US010004591B2

United States Patent
Ichikawa (10) Patent No.: US 10,004,591 B2
(45) Date of Patent: Jun. 26, 2018

(54) INTRAOCULAR LENS

(71) Applicant: CHUKYO MEDICAL CO., INC., Nagoya-shi, Aichi (JP)

(72) Inventor: Kazuo Ichikawa, Nagoya (JP)

(73) Assignee: CHUKYO MEDICAL CO., INC., Nagoya-Shi, Aichi (JP)

( * ) Notice: Subject to any disclaimer, the term of this patent is extended or adjusted under 35 U.S.C. 154(b) by 24 days.

(21) Appl. No.: 14/264,304

(22) Filed: Apr. 29, 2014

(65) Prior Publication Data
US 2015/0305857 A1  Oct. 29, 2015

(51) Int. Cl.
*A61F 2/16* (2006.01)

(52) U.S. Cl.
CPC ........ *A61F 2/16* (2013.01); *A61F 2002/1681* (2013.01); *A61F 2002/1683* (2013.01); *A61F 2002/1689* (2013.01)

(58) Field of Classification Search
CPC .... A61F 2/1629; A61F 2/1632; A61F 2/1635; A61F 2/1605; A61F 2/1608; A61F 2/16015; A61F 2002/1681; A61F 2002/1682; A61F 2002/1683; A61F 2002/1686; A61F 2002/169; A61F 2002/16901; A61F 2002/16902; A61F 2002/16903; A61F 2002/16905; A61F 2002/169051; A61F 2002/169052; A61F 2002/169053
See application file for complete search history.

(56) References Cited

U.S. PATENT DOCUMENTS

| 3,925,825 | A | * | 12/1975 | Richards | .................. A61F 2/16 623/6.41 |
| 4,543,673 | A | * | 10/1985 | Drake | ....................... A61F 2/16 264/1.7 |
| 2002/0116062 | A1 | * | 8/2002 | Portney | ................. A61F 2/1602 623/6.43 |
| 2006/0041308 | A1 | * | 2/2006 | Nichamin | ............. A61F 2/1613 623/6.43 |

FOREIGN PATENT DOCUMENTS

| JP | 58203752 A | 11/1983 |
| JP | 6-48620 U | 7/1994 |
| JP | 2002543920 A | 12/2002 |
| JP | 2003190193 A | 7/2003 |
| JP | 2004515309 A | 5/2004 |

* cited by examiner

*Primary Examiner* — Leslie Lopez
(74) *Attorney, Agent, or Firm* — Bacon & Thomas, PLLC (57) ABSTRACT

Provided is an intraocular lens capable of being reliably fixed into an eye from which an eye lens is extracted without suturing. The intraocular lens includes a pair of nipping portions which is formed at the right and left sides of a lens portion and a leg portion which extends from a limbus of the lens portion or each nipping portion. The nipping portion nips a part of the rear side of an iris inside the eye. A front end of the leg portion comes into contact with the deepest portion of a ciliary sulcus. The intraocular lens is reliably fixed to a rear section without suturing by the nipping of the nipping portion and the contacting of the leg portion.

9 Claims, 10 Drawing Sheets

A-A CROSS SECTION

A-A CROSS SECTION

INTRAOCULAR LENS

BACKGROUND OF THE INVENTION

1. Field of the Invention

The present invention relates to an intraocular lens.

2. Description of the Related Art

As widely known, a surgery operation has been widely performed in which a cloudy white eye lens of a patient is extracted and an intraocular lens is inserted into an eye as the treatment for the eye's cataract. For example, Japanese Patent No. 2792588 below proposes an intraocular lens which is inserted into an eye from which an eye lens is extracted and is sutured to a ciliary body in the treatment of cataract.

SUMMARY OF THE INVENTION

In the technique disclosed in Japanese Patent No. 2792588, the intraocular lens is sutured to the ciliary body. However, it is desirable to use an intraocular lens capable of being fixed into an eye without suturing after an eye lens is extracted in consideration of a patient's burden. For this reason, there is a need to devise a structure (a shape) capable of reliably fixing the intraocular lens into the eye without suturing.

Therefore, an object of the invention is to provide an intraocular lens capable of being reliably fixed into an eye from which an eye lens is extracted without suturing.

In order to solve the above-described problems, according to an aspect of the invention, there is provided an intraocular lens including: a lens portion that is disposed in a rear section of an eye from which at least a part of an eye lens is extracted and serves as the eye lens; a nipping portion that is formed in a shape obliquely extending toward the front side and the lateral side of the lens portion disposed in the rear section and supports the lens portion while nipping a part of a rear section side of an iris of the eye from the rear section; and an extension portion that is formed in a shape extending toward the lateral side of the lens portion and supports the lens portion along with the nipping portion while a portion farthest from the center of the lens portion in the shape comes into contact with the inside of a ciliary sulcus.

Accordingly, the intraocular lens according to the aspect of the invention includes the nipping portion and the extension portion, a part of the rear section side of the iris is nipped by the nipping portion, and the extension portion is brought into contact with the inside of the ciliary sulcus. Accordingly, it is possible to realize the intraocular lens capable of being reliably fixed into the rear section without suturing by the complex fixing methods using the nipping portion and the extension portion.

Further, the extension portion may include a plurality of leg portions that extend in a leg shape from a plurality of positions of a limbus of the lens portion or a limbus of the nipping portion in the circumferential direction toward a direction moving away from the center of the lens portion.

According to the invention, since the extension portion is formed as a plurality of the leg portions having leg shapes, it is possible to realize the intraocular lens capable of being reliably fixed to the rear section by a simple structure and a simple shape.

Further, front ends of the leg portions may be inserted into the ciliary sulcus of the eye so as to come into contact with at least a part of a deep portion of the ciliary sulcus.

According to the invention, since the extension portion is formed as a plurality of the leg portions having leg shapes and the front ends of the leg portions are brought into contact with the inside of the ciliary sulcus, it is possible to reliably fix the intraocular lens to the rear section by using a simple structure with a leg-shaped portion and a simple method of bringing the front end thereof into contact with the inside of the ciliary sulcus in corporation with the nipping of the nipping portion.

Further, the shape of the nipping portion may be a shape in which a portion nipping the iris in the nipping portion is located at the front side inside the eye in relation to the lens portion.

According to the invention, since the shape of the nipping portion is formed in a shape in which a portion nipping the iris is located at the front side inside the eye in relation to the lens portion, it is possible to locate the lens portion at the further rear side while the lens portion is fixed to the rear section inside the eye by the nipping portion (and the extension portion). Accordingly, a sufficient gap may be formed between the lens portion and the iris. Thus, it is possible to effectively suppress the adhesion between the lens portion and the iris.

Further, the extension portion may include an annular ring portion that is inserted into the ciliary sulcus in the circumferential direction.

According to the invention, since the extension portion includes the annular ring portion which is inserted into the ciliary sulcus in the circumferential direction, it is possible to bring the extension portion into contact with the inside of the ciliary sulcus in a wide range of the circumferential direction of the ciliary sulcus when the extension portion is inserted into the ciliary sulcus. Accordingly, it is possible to further reliably fix the intraocular lens to the rear section.

Further, the extension portion may have flexibility and have a size in which at least a part of the extension portion is bent while a portion farthest from the center of the lens portion in the extension portion comes into contact with the inside of the ciliary sulcus of the eye.

According to the invention, the extension portion has flexibility and the size thereof is set to a size in which at least a part of the extension portion is bent while the extension portion is inserted into the ciliary sulcus in a contact state. Accordingly, since the extension portion presses the inside of the ciliary sulcus by a certain degree of force, it is possible to effectively prevent a problem in which the front end of the extension portion is separated from the ciliary sulcus, and hence to reliably fix the intraocular lens to the rear section.

Further, the extension portion may have a bent shape, and the bent shape may be a shape in which the lens portion is movable in the front and rear direction inside the eye in response to the movement of the ciliary sulcus while the portion farthest from the center of the lens portion in the extension portion comes into contact with the inside of the ciliary sulcus of the eye.

According to the invention, the extension portion has a shape in which the lens portion moves in the front and rear direction inside the eye in response to the movement of the ciliary body while the extension portion is fixed to the ciliary sulcus. Thus, when a patient moves the ciliary body for the focusing operation of the eye, the lens portion moves in the front and rear direction in response to the movement. Accordingly, there is a possibility of realizing the intraocular lens capable of performing the focusing operation of the eye in response to the distance to the object.

Further, each leg portion may include a bent portion that is bent at a position between an end close to the lens portion and an end far from the lens portion in the leg shape, and each leg portion may have a shape in which an end close to the lens portion in the leg portion is located at the front side of the eye in relation to the bent portion and an end far from the lens portion in the leg portion is located at the front side of the eye in relation to the bent portion so that the lens portion is pressed toward the front side inside the eye when the ciliary sulcus presses the leg portion while the lens portion is disposed at the rear section of the eye.

According to the invention, the shape of the leg portion is specifically formed as a shape in which the leg portion extends from a position close to the lens portion toward the rear side inside the eye and is bent so as to extend toward the front side inside the eye. Since such a bent shape is formed, when the patient moves the ciliary sulcus in order to perform the focusing operation of the eye, the lens portion moves in the front and rear direction in response to the movement. Accordingly, it is possible to realize the intraocular lens capable of performing the focusing operation of the eye in response to the distance to the object.

Further, a portion coming into contact with the inside of the ciliary sulcus in the extension portion may be provided with a concave portion or a convex portion fitted to an uneven portion inside the ciliary sulcus.

According to the invention, since a portion coming into contact with the inside of the ciliary sulcus in the extension portion is provided with the concave portion or the convex portion to be fitted to the uneven portion inside the ciliary sulcus, it is possible to further reliably fix the extension portion into the ciliary sulcus by the fitting with respect to the ciliary sulcus through the uneven portion.

Further, the intraocular lens may include a sub-extension portion that portion so as to come into contact with a surface of a ciliary body.

According to the invention, since the sub-extension portion which extends from the side surface of the extension portion or the limbus of the lens portion and comes into contact with the surface of the ciliary body is also provided in addition to the nipping portion nipping the iris and the extension portion coming into contact with the inside of the ciliary sulcus, the intraocular lens is further reliably fixed into the eye and hence may be reliably fixed into the eye without suturing.

Further, the sub-extension portion may have a shape in which the sub-extension portion extends from the side surface of the extension portion or the limbus of the lens portion toward the rear side inside the eye so that a force of pressing the lens portion toward the front side inside the eye is transmitted to the sub-extension portion when the sub-extension portion is pressed by the ciliary body while the lens portion is disposed at the rear section of the eye.

According to the invention, the sub-extension portion which comes into contact with the surface of the ciliary body extends from the side surface of the extension portion or the limbus of the lens portion toward the rear side inside the eye. Accordingly, when the sub-extension portion is pressed by the ciliary body, a force of pressing the lens portion toward the front side inside the eye is transmitted thereto. Thus, when the patient moves the ciliary body in order to perform the focusing operation of the eye, the lens portion moves in the front and rear direction in response to the movement. As a result, it is possible to realize the intraocular lens capable of performing the focusing operation of the eye in response to the distance to the object.

DETAILED DESCRIPTION OF THE PREFERRED EMBODIMENTS

Figure 1:
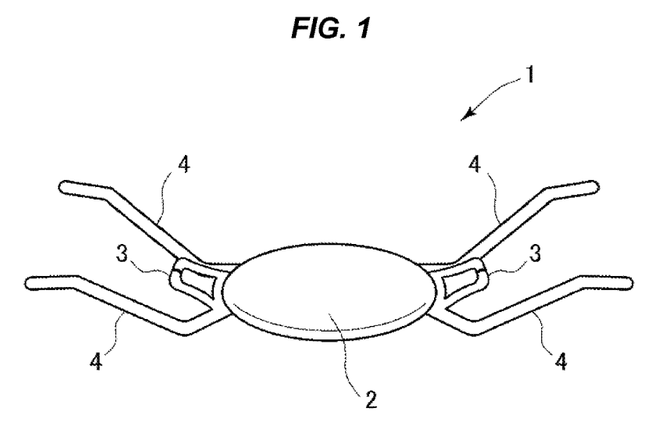
FIG. 1 is a perspective view illustrating an intraocular lens of a first embodiment of the invention.
Figure 2:
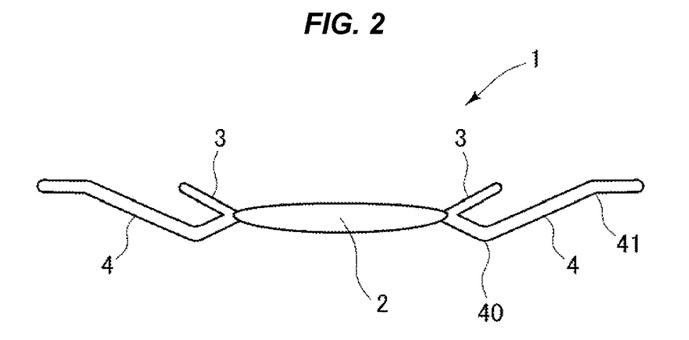
FIG. 2 is a side view illustrating the intraocular lens of the first embodiment.
Figure 3:
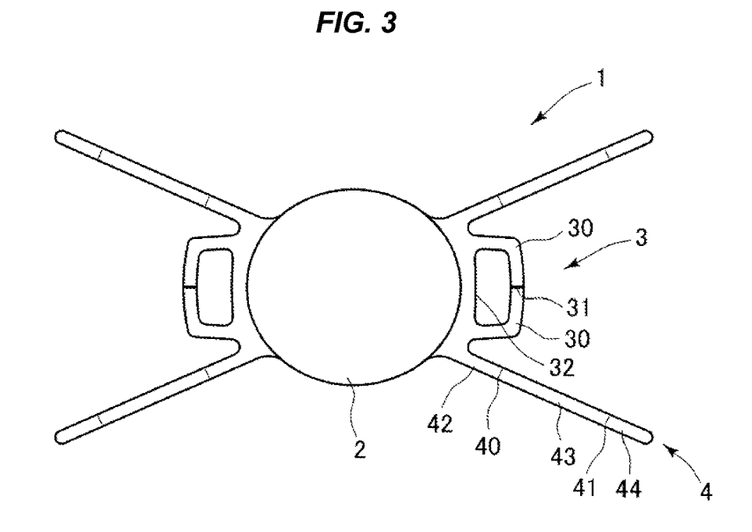
FIG. 3 is a front view illustrating the intraocular lens of the first embodiment.

Hereinafter, embodiments of the invention will be described with reference to the drawings. First, FIGS. 1 to 3 illustrate an intraocular lens 1 of an embodiment of the invention. FIG. 1 is a perspective view of the intraocular lens 1, FIG. 2 is a side view thereof, and FIG. 3 is a front view thereof (the description on the direction such as a side surface or a front surface indicates the direction (the side surface or the front surface) of a patient's face (or eye) in which an intraocular lens is fixed into an eye.

The intraocular lens 1 includes a lens 2, a nipping portion 3, and a leg portion 4 (an extension portion). The lens 2 is disposed in a rear section of an eye (a section behind an iris)

after an eye lens becoming cloudy white due to, for example, the cataract is extracted from the patient's eye, and serves as the eye lens.

The nipping portion 3 supports and fixes the lens 2 in the rear section by nipping the iris therebetween. The nipping portion 3 includes a pair of arms 30 and 30. As illustrated in FIG. 2, the arms 30 and 30 extend from both right and left limbuses of the lens 2 and are curved at the half portion thereof. Here, the arms are formed so that front ends 31 and 31 of both arms 30 and 30 contact each other when the iris is not nipped therebetween.

The nipping portion 3 is formed of a material having elasticity (flexibility and bendability). Here, a doctor (an operator) may elastically deform the nipping portion 3 so that a part of a portion contacting the rear section of the iris is nipped between the front ends 31 and 31 of the arms 30 and 30. Accordingly, the iris is continuously nipped between the arms 30 and 30 due to the elastic restoration force thereof. When the same nipping operation is performed by the nipping portions 3 formed at the right and left sides of the intraocular lens 1 in the drawing, the lens 2 is supported in the rear section.

As illustrated in FIG. 2, the pair of arms 30 and 30 of the nipping portion 3 may have a shape in which the arms obliquely extend from the lens 2 toward the front side of the eye (that is, the front ends 31 of the arms 30 and 30 are located at the front side in relation to the root side) (as described above, the description on the front side or the rear side also indicates the front side or the rear side of the patient's face in which the intraocular lens 1 is attached into the eye). Accordingly, a gap may be formed between the lens 2 and the iris as will be described later. This exhibits an important effect of preventing (suppressing) the adhesion between the lens 2 and the iris.

In the embodiment of FIGS. 1 to 3, the leg portion 4 has a structure with four legs. Each of the four legs includes bent portions 40 and 41, a root portion 42 which is located near the lens 2 in relation to the bent portion 40, an intermediate portion 43 which is located between the bent portions 40 and 41, and a front end 44 which is located near the front end in relation to the bent portion 41. As illustrated in FIG. 2, the root portion 42 has a shape in which the root portion extends backward in relation to the lens 2 (the bent portion 40 is located at the rear side in relation to the lens 2). The intermediate portion 43 has a shape in which the intermediate portion extends from the bent portion 40 toward the front side of the eye (the bent portion 41 is located at the front side inside the eye in relation to the bent portion 40). The front end 44 has a shape in which the front end extends (substantially) in parallel to the lens.

Furthermore, the leg portion 4 of FIGS. 1 to 3 is mere an example. As will be described later, in the invention, the leg portion 4 may have various shapes. The nipping portion 3 and the leg portion 4 may be formed of, for example, a resin material or the like so as to be integrated with the lens 2. Alternatively, the nipping portion and the leg portion may be formed separately from the lens 2 and then may be coupled (stuck) to each other.

Figure 4:
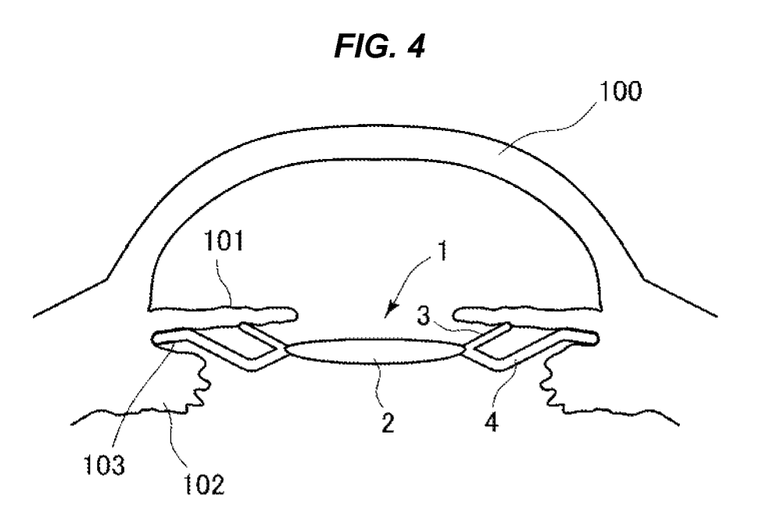
FIG. 4 is a view illustrating a state where the intraocular lens is inserted and fixed into an eye.

FIG. 4 illustrates a cross-sectional view of an eye in which the intraocular lens 1 of FIGS. 1 to 3 is attached (fixed). As widely known, the front side of an iris 101 inside the eye is called the front section and the rear side thereof is called the rear section. Here, the intraocular lens 1 is disposed at the rear section between the both sections. A ciliary body 102 exists at the rear side of the iris 101, and the eye lens is generally supported at the center side of the ciliary body 102 inside the eye. A groove-shaped area which is continuously formed between the iris 101 and the ciliary body 102 in the circumferential direction is called a ciliary sulcus 103.

In the state where the entire eye lens is extracted due to the cataract, a part of a cornea 100 is incised, and the intraocular lens 1 is inserted from the incision toward the rear section. At that time, for example, the intraocular lens 1 is inserted into the eye while being rolled in a cartridge by using the elasticity (bendability) of the intraocular lens 1, the front end of the cartridge is pressed to the rear section through the cornea 100, and the intraocular lens 1 is discharged thereto.

In the case where the intraocular lens 1 is fixed to the rear section, the iris is nipped by the nipping portion 3, and the leg portion 4 is inserted and fixed into the ciliary sulcus 103. At the portion near the nipping portion 3, a part of the rear surface of the iris is nipped by the arms of the right and left nipping portions 3 and 3. Further, at the portion near the leg portion 4, the front end of the leg portion 4 is fixed to the deepest portion of the ciliary sulcus 103 in a contact state. Furthermore, regarding the contact of the front end of the leg portion 4, the contact portion may not be essentially the deepest portion of the ciliary sulcus 103. For example, the front end may come into contact with at least a part inside the ciliary sulcus 103.

As the main point of the invention, any portion of the intraocular lens 1 including the nipping portion 3 and the leg portion 4 is not sutured into the eye. Further, the length of the leg portion 4 may be designed so that the leg portion 4 is slightly bent while the front end of the leg portion 4 is inserted into the ciliary sulcus 103. By the above-described complex fixing method using two kinds of fixing means of the nipping portion and the leg portion, the intraocular lens 1 is reliably fixed to the rear section.

The intraocular lens 1 of the invention has a function capable of moving the position of the lens 2 in the front and rear direction by the action (the reflex action) in which the patient's eye tries to focus on an object. The function will be described with reference to FIG. 5.

Figure 5:
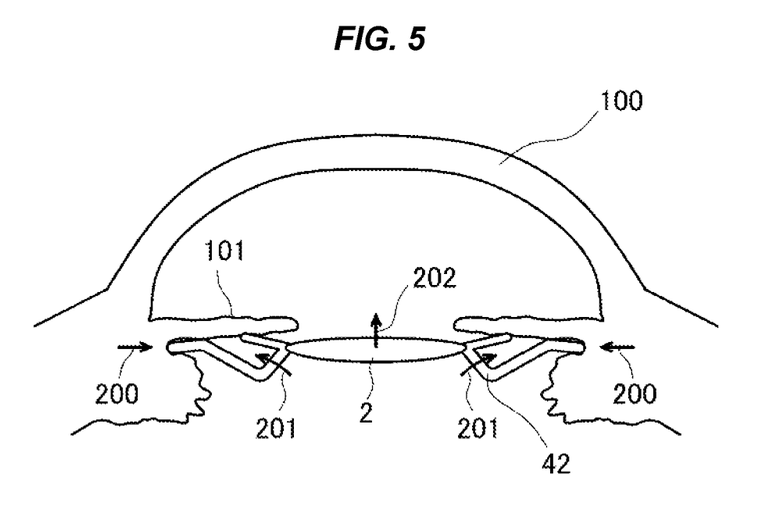
FIG. 5 is a side view illustrating an example of a state where the intraocular lens moves.

According to the medical knowledge, a force is exerted in the direction indicated by the arrow 200 of FIG. 5 in the case where a human's eye tries to focus on an object. This force twists the leg portion 4 of the intraocular lens 1 as illustrated in FIG. 5. That is, the bent portion 41 is pressed toward the lens 2, and the root portion 42 and the intermediate portion 43 of the leg portion 4 change to a posture in which the root portion 42 and the intermediate portion 43 become more perpendicular to the lens 2.

Accordingly, the posture of the root portion 42 changes in the direction of the arrow 201, and hence the lens 2 is pressed toward the front side inside the eye. When the force of the arrow 200 disappears, the lens 2 returns to the original position. In this way, when the lens 2 moves in the front and rear direction, the distance with respect to a visual object formed as a clear image on a retina by the lens 2 also changes. Accordingly, the patient with the intraocular lens 1 may focus on and see not only an object in a single distance, but also an object within any distance range from himself or herself.

FIGS. 6 to 10 illustrate different embodiments of the intraocular lens of the invention. Furthermore, in the embodiments below, the same reference numerals will be given to the same components as those of FIGS. 1 to 3, and the repetitive description thereof will not be presented.

Figure 6:
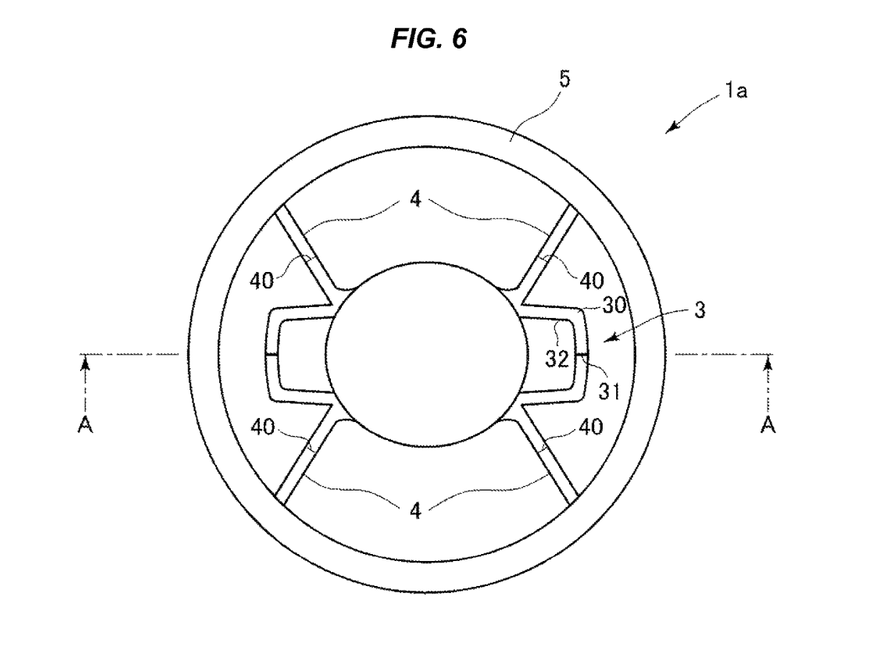
FIG. 6 is a front view illustrating an intraocular lens of a second embodiment.
Figure 7:
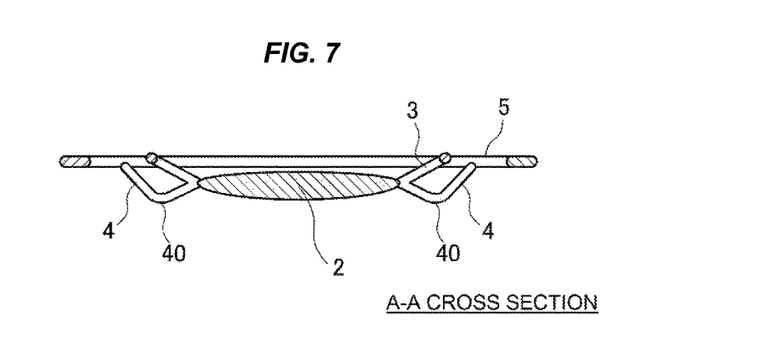
FIG. 7 is a cross-sectional view illustrating the intraocular lens of the second embodiment.

An intraocular lens 1a of a second embodiment of FIGS. 6 and 7 is an example in which a ring portion 5 is formed in the circumferential direction so that the front ends of the leg portions 4 are connected to the ring portion. In this example, the leg portion includes the bent portion 40 as in the case of FIG. 1 and the like. Here, the leg portion 4 first extends from the limbus of the lens 2 or the nipping portion 3 toward the rear side inside the eye, and is bent at the bent portion 40 so as to be directed toward the ring portion 5 located at the front side inside the eye.

As illustrated in FIG. 7, the ring portion 5 has a cross-sectional shape in which the ring portion is short and flat in the visual axis direction (for example, the up and down direction of FIG. 2) of the eye. The intraocular lens 1a of the second embodiment of FIGS. 6 and 7 may be disposed such that a part of the rear surface of the iris is nipped by the nipping portion 3, the ring portion 5 is inserted into the ciliary sulcus 103 along the entire circumference thereof, and the outer end of the ring portion 5 in the radial direction comes into contact with, for example, the deepest portion of the ciliary sulcus 103. Since the ring portion 5 comes into contact with the ciliary sulcus along the entire circumference thereof, the ring portion is stably fixed. At that time, it is desirable that the ring portion 5 has a flat shape in that the ring portion may be suitably inserted into the ciliary sulcus.

Figure 8:
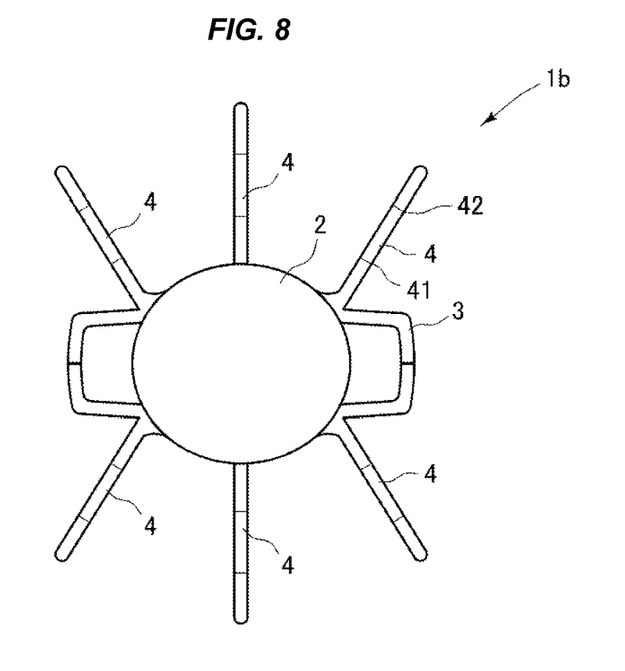
FIG. 8 is a front view illustrating an intraocular lens of a third embodiment.

FIG. 8 illustrates an intraocular lens 1b of a third embodiment. The example of FIG. 8 is an example in which six leg portions 4 are provided. Even in this example, the front ends of the six leg portions 4 are inserted and fixed into the deepest portion of the ciliary sulcus. The invention is not limited to the case where the four leg portions 4 are provided as illustrated in FIG. 1 and the six leg portions 4 are provided as illustrated in FIG. 8. For example, an arbitrary (even) number of the leg portions 4 such as eight or ten leg portions may be provided.

Figure 9:
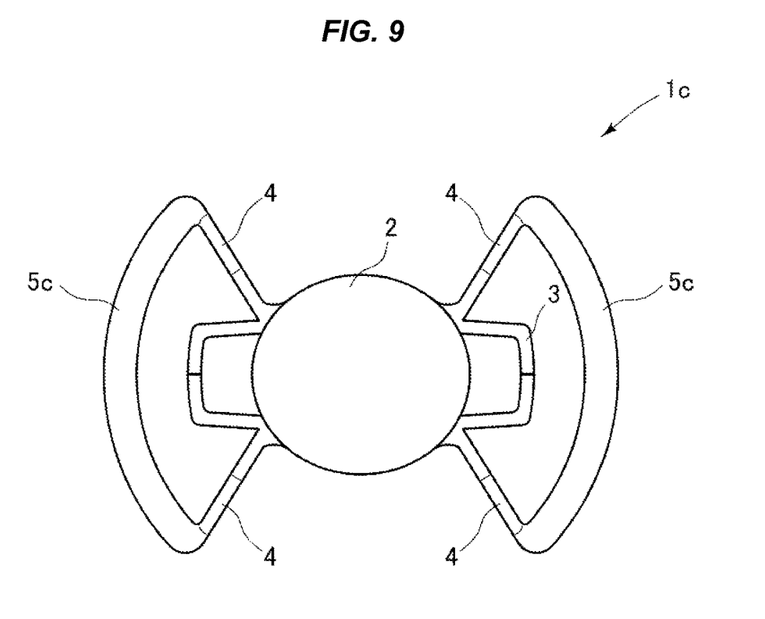
FIG. 9 is a front view illustrating an intraocular lens of a fourth embodiment.

FIG. 9 illustrates an intraocular lens 1c of a fourth embodiment. The intraocular lens 1c is an example in which the ring portion 5 of FIG. 5 is not formed in the entire circumference. In this example, a circular-arc portion 5c is formed so as to connect the front ends of the leg portions 4 which are adjacent to each other at both right and left sides of the nipping portion 3. The invention is not limited to this example. For example, in the invention, only a part of the ring portion of FIG. 6 may be formed.

Figure 10:
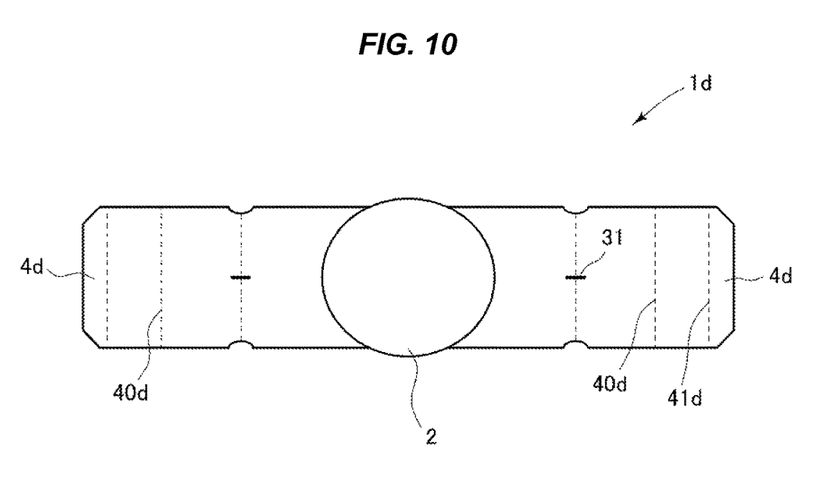
FIG. 10 is a front view illustrating an intraocular lens of a fifth embodiment.

FIG. 10 illustrates an intraocular lens 1d of a fifth embodiment. The intraocular lens 1d has a structure in which the leg portion and the nipping portion are commonly used. Specifically, a plate-shaped portion 4d which has substantially the same width as the lens 2 and has a thin plate shape (a flat shape) in the thickness direction (the visual axis direction) is provided at each of the right and left sides of the lens 2. A notched portion 31 is provided in the vicinity of the middle position of the plate-shaped portion 4d, and nips the rear side of the iris so that a nipping portion is formed. Further, the front end side of the plate-shaped portion 4d corresponds to the leg portion, and the front end comes into contact with, for example, the deepest portion of the ciliary sulcus. That is, the intraocular lens of the invention includes a plate-shaped portion which is commonly used as the extension portion and the nipping portion. Here, the nipping portion is the notched portion which is formed at the intermediate portion (which may not be limited to the middle position) of the plate-shaped portion so as to nip the iris, and the front end of the plate-shaped portion may come into contact with the inside of the ciliary sulcus.

The plate-shaped portion 4d may have a shape in which a flat plate is bent at three positions. That is, in FIG. 10, the dashed line intersecting the notched portion 31 is a bending line which protrudes toward the front side inside the eye, the dashed line 40d is a bending line which protrudes toward the rear side inside the eye, and the dashed line 41d is a bending line which protrudes toward the front side inside the eye. Then, the front end side of the dashed line 41d may extend in the transverse direction (the direction perpendicular to the visual axis).

With the above-described shape, since the notched portion 31 protrudes toward the front side inside the eye, the iris may be easily nipped and the front end side of the dashed line may be easily inserted into the ciliary sulcus. Further, since the bending lines are provided at three positions, the lens 2 moves forward when the force of the arrow 200 is exerted similarly as illustrated in FIG. 5 above, and the lens 2 returns backward as the force disappears. In the case of the shape of FIG. 10, since the leg portion is formed in a thick size, the strength is improved.

Figure 11:
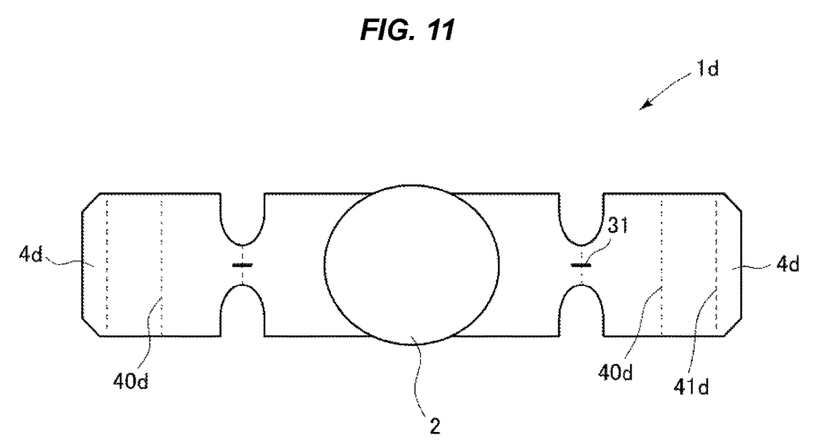
FIG. 11 is a front view illustrating an intraocular lens of a sixth embodiment.

The intraocular lens 1d of FIG. 10 may be deformed as illustrated in FIG. 11. In a sixth embodiment of FIG. 11, the plate-shaped portion 4d is formed in a shape in which the periphery of the notched portion 31 is deeply recessed. In the case of this shape, since it is possible to prevent an unnecessary portion from contacting the iris or to easily bend the notched portion 31, a nipping operation is reliably performed by the notched portion 31.

In the intraocular lens of the invention, the front end shape of the leg portion may be various. FIGS. 12 to 15 illustrate four examples of the front end shape of the leg portion.

Figure 12:
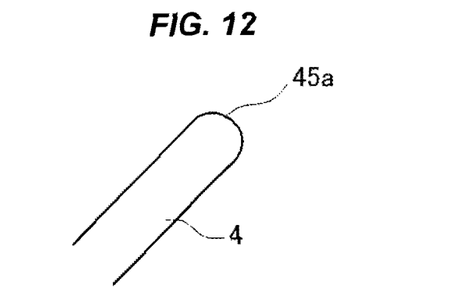
FIG. 12 is a view illustrating a first example of a front end of a leg portion.
Figure 13:
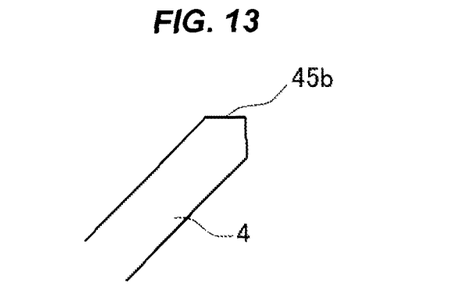
FIG. 13 is a view illustrating a second example of the front end of the leg portion.

In the example of FIG. 12, a front end 45a of the leg portion 4 has a curved surface shape. In this example, the curved surface comes into plane-contact with the deepest portion (the inside) of the ciliary sulcus, and hence the leg portion 4 is reliably fixed to the ciliary sulcus. In the example of FIG. 13, a front end 45b of the leg portion 4 is formed in a sharp shape with a corner. In this example, the corner is pressed against the deepest portion (the inside) of the ciliary sulcus, and hence the leg portion 4 is reliably fixed to the ciliary sulcus.

Figure 14:
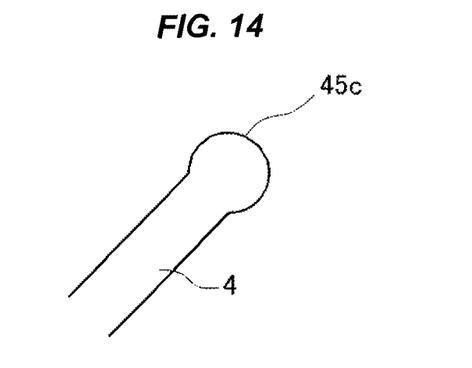
FIG. 14 is a view illustrating a third example of the front end of the leg portion.
Figure 15:
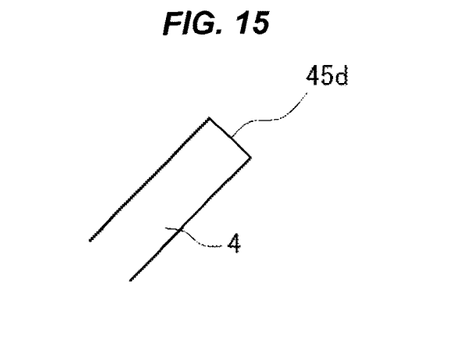
FIG. 15 is a view illustrating a fourth example of the front end of the leg portion.

In the example of FIG. 14, a front end 45c of the leg portion 4 is formed in a spherical shape. In this example, the front end comes into plane-contact with the deepest portion (the inside) of the ciliary sulcus by the spherical shape thereof, and hence the leg portion 4 is reliably fixed to the ciliary sulcus. In the example of FIG. 15, a front end 45d of the leg portion 4 is formed in a plane shape. In this example, the front end comes into plane-contact with the deepest portion (the inside) of the ciliary sulcus by the plane shape thereof, and hence the leg portion 4 is reliably fixed to the ciliary sulcus.

Furthermore, the leg portions 4 of FIGS. 12 to 15 may have plate shapes (flat shapes), and only the surfaces perpendicular to the visual axis may be illustrated in FIGS. 12 to 15. In that case, for example, the front end 45b of FIG. 13 comes into line-contact with the deepest portion of the ciliary sulcus.

In the intraocular lens of the invention, the front end shape of the leg portion may be further modified as below. This modification will be described with reference to FIGS. 16 to 18.

Figure 16:
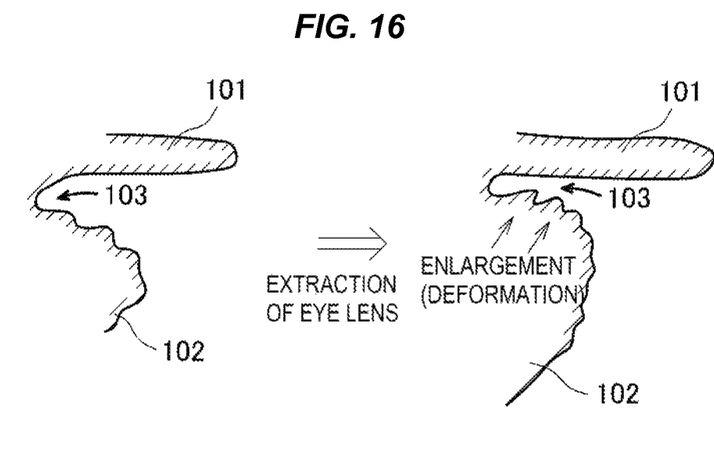
FIG. 16 is a view illustrating an example of the state of a ciliary body and a ciliary sulcus after an eye lens is extracted.

According to the new knowledge obtained by the inventor, there is a tendency that the ciliary body 102 is enlarged (deformed) after the eye lens is extracted. In the enlargement (deformation), for example, as illustrated in FIG. 16, the ciliary sulcus 103 is deformed so as to be narrowed. Accordingly, the uneven shape which exists on the surface of the ciliary sulcus becomes closer to the iris 101.

Figure 17:
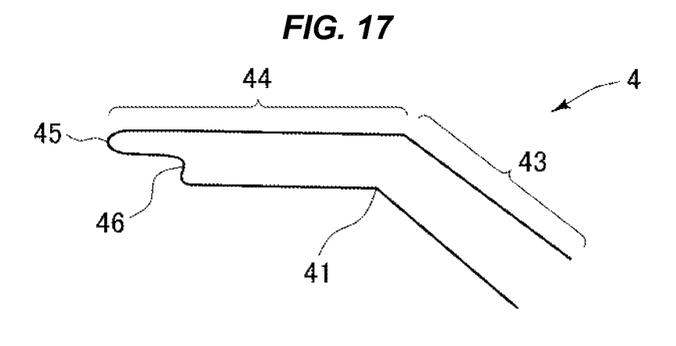
FIG. 17 is a view illustrating an example of a concave portion of the front end of the leg portion.

In order to handle this deformation (or use this deformation), it is desirable to form a concave portion 46 in the vicinity of the front end 45 of the leg portion 4 as illustrated in FIG. 17. The formation position of the concave portion 46 becomes a position opposite to the iris (a position facing the ciliary body) in the leg portion 4 when the leg portion is fixed into the eye. That is, the formation position may be a position close to the front end in a degree that the concave portion comes into contact with the enlarged (deformed) ciliary sulcus.

Figure 18:
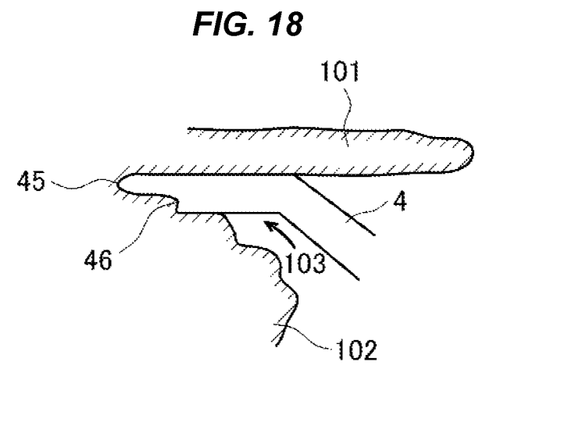
FIG. 18 is a view illustrating a function of the concave portion of the front end of the leg portion.

Accordingly, as illustrated in FIG. 18, a convex portion of the ciliary body 102 is inserted into the concave portion 46 of the leg portion 4, and hence the leg portion 4 is further reliably fixed to the ciliary sulcus. Even in the leg portions of FIGS. 1 and 12 to 15, the leg portion 4 having a different shape, the ring portion of FIG. 7, or the circular-arc portion of FIG. 9, the concave portion 46 may exhibit the function illustrated in FIG. 18 when the concave portion is formed in (the vicinity of) the front end of the leg portion. Further, the invention is not limited to the case of forming the concave portion. For example, an uneven portion (or a concave portion and a convex portion) may be formed so as to be fitted to the uneven shape inside the ciliary sulcus 103.

In the above-described intraocular lens, the structure (the leg portion, the ring portion, and the like) coming into contact with the inside of the ciliary sulcus is formed, but the intraocular lens of the invention is not limited thereto. For example, a structure coming into contact with the ciliary body may be formed. The example is illustrated in FIGS. 19 to 25.

Figure 19:
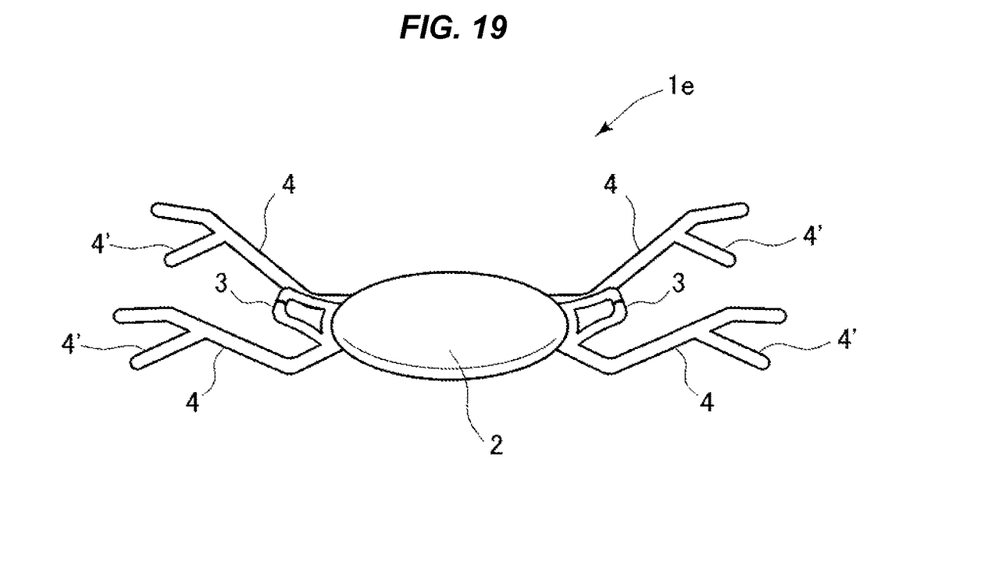
FIG. 19 is a perspective view illustrating an intraocular lens of a seventh embodiment.
Figure 20:
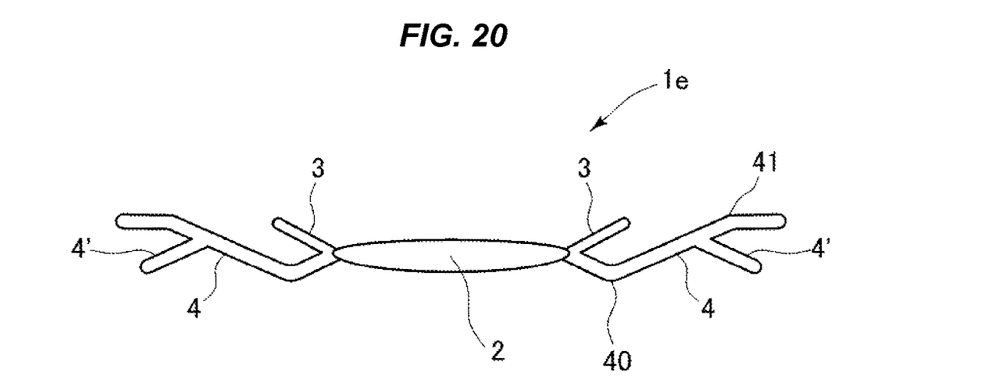
FIG. 20 is a side view illustrating the intraocular lens of the seventh embodiment.

FIG. 19 is a perspective view illustrating an intraocular lens 1e of a seventh embodiment, and FIG. 20 is a side view thereof. The intraocular lens 1e includes a sub-leg portion 4' which is divided from the side surface of the intermediate portion 43 of the leg portion 4 and obliquely extends toward the rear side inside the eye. The front view of the intraocular lens 1e may be, for example, the shape of FIG. 3. That is, the extension direction when viewed from the front surface of the sub-leg portion 4' may be the same direction as that of the leg portion 4. Alternatively, the extension direction when viewed from the front surface of the sub-leg portion 4' may be different from the extension direction of the leg portion 4. Further, the invention is not limited to the case where the sub-leg portion 4' has the structures of FIGS. 19 and 20. For example, the sub-leg portion may be divided from a certain portion of the leg portion 4 or may extend from the limbus of the lens 2.

Figure 21:
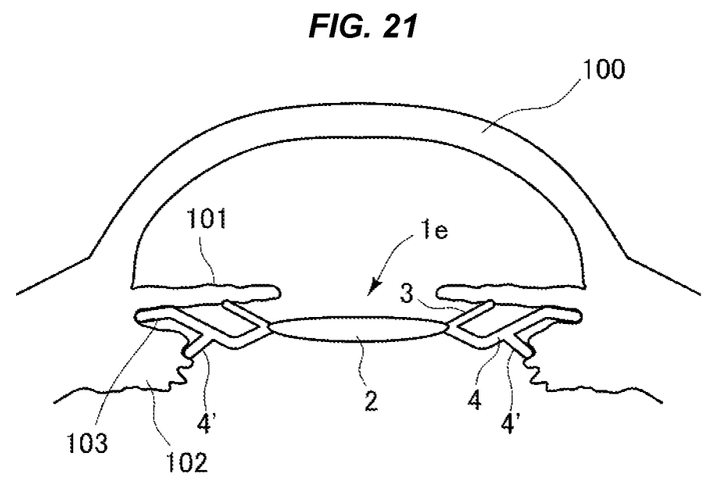
FIG. 21 is a view illustrating a state where the intraocular lens of the seventh embodiment is inserted and fixed into an eye.

An example in which the intraocular lens 1e is attached into the eye is illustrated in FIG. 21. As described above, the nipping portion 3 nips a part of the iris, the front end 44 of the leg portion 4 comes into contact with the inside of the ciliary sulcus 103, and the front end of the sub-leg portion 4' comes into contact with the ciliary body 102. As described above, since there is a tendency that the ciliary body 102 is enlarged after the eye lens is extracted, the front end of the sub-leg portion 4' reliably comes into contact with the surface of the ciliary body 102. As a result, the intraocular lens 1e is fixed into the eye (the rear section) in a complex manner in which the iris 101 is nipped by the nipping portion 3, the leg portion 4 comes into contact with the inside of the ciliary sulcus 103, and then the sub-leg portion 4' comes into contact with the ciliary body 102.

Figure 22:
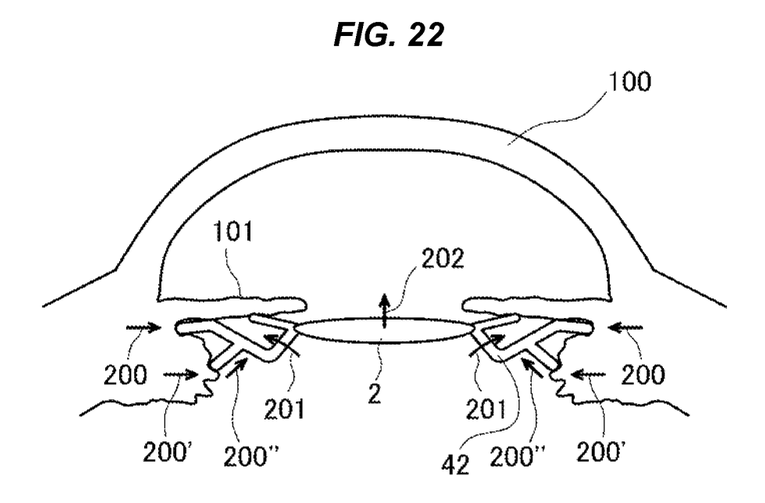
FIG. 22 is a side view illustrating an example of a state where the intraocular lens of the seventh embodiment moves.

The intraocular lens 1e further improves the patient's focusing function by forming the sub-leg portion 4'. The shape is illustrated in FIG. 22. According to the knowledge of the inventor, in a case where the patient having the intraocular lens 1e attached into the eye wants to focus on an object, a force 200' is also exerted on the ciliary body 102 in addition to the force exerted in the direction of the arrow 200 described above. The force 200' presses the sub-leg portion 4' in the direction of the arrow 200" in the drawing.

Such an action is synthesized with the action in which the force 200 presses the leg portion 4 as described above, the leg portion 4 is twisted, and hence the posture of the root portion 42 of the leg portion 4 is largely changed in the direction of the arrow 201. Accordingly, the lens 2 is largely pressed into the front side inside the eye. When the forces of the arrows 200 and 200' disappear, the lens 2 returns to the original position.

That is, not only the movement of the ciliary sulcus 103, but also the movement of the ciliary body 102 are transmitted to the intraocular lens 1e, and hence the lens 2 moves in the front and rear direction. Then, the movement amount of the lens 2 in the front and rear direction may be increased compared to the case where only the movement of the ciliary sulcus 103 is transmitted to the intraocular lens. Further, according to the knowledge of the inventor, the expansion and contraction of the ciliary body is relatively larger than that of the ciliary sulcus. Accordingly, the movement amount of the lens 2 in the front and rear direction in the intraocular lens 1e increases due to the formation of the sub-leg portion 4'.

When the movement range of the lens 2 in the front and rear direction further increases, it is possible to largely change even the distance with respect to a visual object formed as a clear image on a retina by the lens 2. Thus, the patient having the intraocular lens 1e attached to the eye may focus on and see an object within a relatively large distance range from himself or herself.

Figure 23:
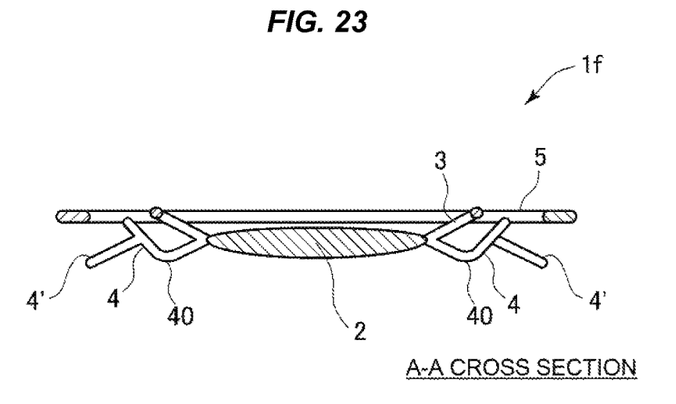
FIG. 23 is a cross-sectional view illustrating an intraocular lens of an eighth embodiment.

The structure in which the intraocular lens of the invention comes into contact with the ciliary body 102 is not limited to the above-described example, and any structure in which the intraocular lens comes into contact with the ciliary body 102 may be used. For example, the sub-leg portion 4' may be added to the intraocular lens 1a of FIGS. 6 and 7. An eighth embodiment which employs such a structure is illustrated in FIG. 23. FIG. 23 is a cross-sectional view of an intraocular lens 1f of the eighth embodiment taken along the line A-A and corresponding to FIG. 7.

The front view of the intraocular lens 1f may be the similar shape of FIG. 6. That is, the extension direction when viewed from the front surface of the sub-leg portion 4' may be the same as the extension direction of the leg portion 4. Alternatively, the extension direction when viewed from the front surface of the sub-leg portion 4' may be different from the extension direction of the leg portion 4. In the intraocular lens 1f, as described above, the nipping portion 3 nips a part of the iris, the ring portion 5 comes into contact with the inside of the ciliary sulcus along the circumferential direction, and the front end of the sub-leg portion 4' comes into contact with the ciliary body. With such a complex structure, the intraocular lens is reliably fixed into the eye.

Figure 24:
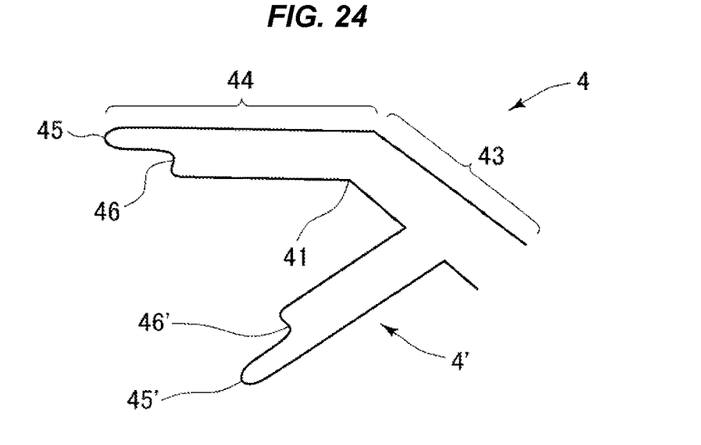
FIG. 24 is a view illustrating an example of a concave portion of a front end of a sub-leg portion.
Figure 25:
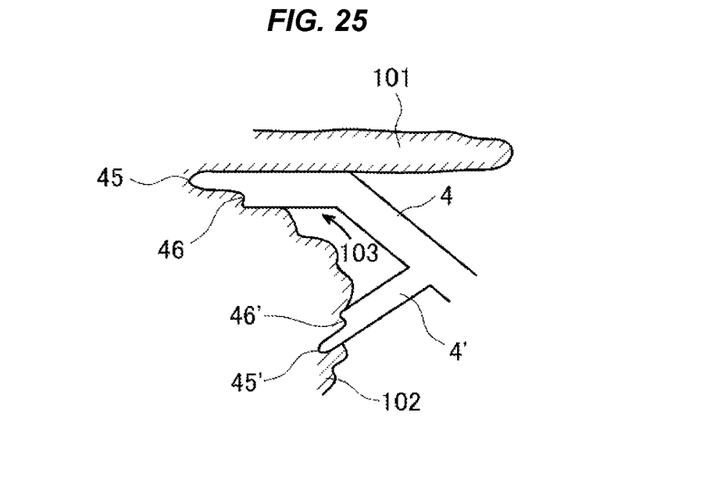
FIG. 25 is a view illustrating the function of the concave portion of the front end of the sub-leg portion.

The concave portion (the convex portion or the uneven portion) formed in the front end of the leg portion 4 illustrated in FIGS. 17 and 18 may be formed in the front end of the sub-leg portion 4'. Such an example is illustrated in FIGS. 24 and 25. In the example of FIG. 24, a concave portion 46' is formed in the vicinity of a front end 45' of the sub-leg portion 4'. The concave portion 46' may be formed in the front end of the sub-leg portion 4' of each of the intraocular lenses 1e and 1f.

Accordingly, when the intraocular lens is attached into the eye, as illustrated in FIG. 25, the convex portion of the ciliary body 102 is inserted into the concave portion 46' of the sub-leg portion 4', and hence the sub-leg portion 4' is reliably fixed to the surface of the ciliary body 102. The formation target of the concave portion 46' is not limited to the above-described intraocular lenses 1e and 1f, and the concave portion may be formed in the front end of the contact portion with respect to the ciliary body in the intraocular lens. Further, the invention is not limited to the case where the single concave portion 46' is formed, but an uneven shape (for example, a plurality of concave portions and a plurality of convex portions) may be formed so as to be fitted to the uneven shape of the surface of the ciliary body 102.

The above-described embodiments of the invention may be appropriately modified without departing from the spirit of claims. For example, the shape and the structure of the nipping portion are not limited to the example of the above-described arm shape, but a shape and a structure may be employed in which at least a part of the rear section side of the iris 101 is nipped and a gap is formed between the lens 2 and the iris 101. Further, the shape of the leg portion 4 is formed so that the leg portion is bent at two positions in the above-described embodiments, but the invention is not limited thereto. For example, a shape may be employed in which the leg portion is bent at more positions (three positions, four positions, or the like). Alternatively, the bending direction may be set to be different from the above-described bending direction. Further, the bent portion may not be bent with a corner, but may be bent in a curve shape (an R-shape).

Further, in the description above, a structure has been described in which the nipping portion 3, the extension portion (the leg portion 4 and the ring portion 5), and the sub-extension portion 4' are provided together, but in the invention, only some of the components or only a certain combination thereof may be provided. For example, a configuration may be employed in which the nipping portion 3 is not provided and only the extension portion (the leg portion 4 and the ring portion 5) is provided. Such a shape may be obtained just by removing the nipping portion 3 in FIGS. 1 to 10.

What is claimed is:

1. An intraocular lens comprising:
   a lens portion configured for placement in a rear section of a human eye from which at least a part of an eye lens of the human eye is extracted, wherein the lens portion is configured to serve an optical function previously provided by the eye lens;
   nipping portions, each having flexibility and configured to obliquely extend from (i) an outer periphery of the lens portion toward a front side of the lens portion, through which an optical axis passes, and (ii) a lateral side of the lens portion extending between the nipping portions, the nipping portions configured to support the lens portion and to nip a part of a rear side of an iris of the human eye from its rear section in a way such hat the nipping portions form a gap between the iris and the lens portion when the intraocular lens is implanted in the eye; and
   extension portions defined by first and second groups of multiple leg portions, said first group of multiple leg portions being provided on one side of a limbus of the lens portion and said second group of multiple leg portions being provided on another side of the limbus of the lens portion, said multiple leg portions of each group extending away from the lateral side of the lens portion and from the limbus of the lens portion or extending away from a limbus of one of the nipping portions and toward a direction away from a center of the lens portion and each of the multiple leg portions along with the nipping portions configured to support the lens portion,
   wherein each leg portion has flexibility and includes a first bent portion, a second bent portion, a linear root portion, a linear intermediate portion, and a linear front end portion,
   wherein the linear root portion extends backward from a back side of the lens portion and away from the lateral and the back sides from the limbus of the lens portion to the first bent portion;
   the linear intermediate portion extends from the first bent portion forward and away from the back side, past the front side, and away from the lateral side to the second bent portion, and
   the linear front end portion extends from the second bent portion substantially parallel to the lens portion and away from the lateral side of the lens portion; and
   wherein the fron end portion of each leg portion is configured to bend and come into contact with an inside of a ciliary sulcus of the human eye when the intraocular lens is placed in the rear section of the human eye.

2. The intraocular lens according to claim 1,
   wherein each nipping portion includes a pair of arm members configured for nipping the iris and configured to be located at the front side of the lens portion.

3. The intraocular lens according to claim 1,
   wherein each leg portion is configured such that the lens portion is movable in a front direction and a rear direction inside the human eye in response to a movement of the ciliary sulcus when the front end portion of each leg portion comes into contact with the inside of the ciliary sulcus of the human eye.

4. The intraocular lens according to claim 1,
   wherein the front end portion of each leg portion is provided with a concave portion or a convex portion adapted to be fitted to an uneven portion inside the ciliary sulcus.

5. The intraocular lens according to claim 1, further comprising:
   a sub-extension portion that extends from a side surface of each leg portion so as to come into contact with a surface of the ciliary sulcus.

6. The intraocular lens according to claim 5,
   wherein each sub-extension portion has a shape in which the respective sub-extension portion extends from the respective side surface toward the rear section inside the eye so that a force of pressing the lens portion toward a front section inside the eye is transmitted to the respective sub-extension portion when the respective sub-extension portion is pressed by the ciliary sulcus while the lens portion is disposed at the rear section of the eye.

7. An intraocular lens comprising:
   a lens portion configured for placement in a rear section of a human eye from which at least a part of an eye lens of the human eye is extracted, wherein the lens portion is configured to serve an optical function previously provided by the eye lens when implanted in the eye;
   a first nipping portion on a first side of the lens portion and a second nipping portion on a second side of the lens portion, each nipping portion having a first arm and a second arm that extend from an outer periphery of the lens portion toward a front side and away from a lateral side of the lens portion and configured to support the lens portion and configured to nip a part of a rear section side of an iris of the human eye from the rear section, wherein the first and second nipping portions are configured in a way such that a hap is formed between the iris of the human eye and the lens portion, when the intraocular lens is placed in the rear section of the human eye; and a first leg portion, a second leg portion, a third leg portion, and a fourth leg portion, each of said leg portions extending away from the lateral side of the lens portion from a limbus of the lens portion or a limbus of a respective nipping portions and toward a direction away from a center of the lens portion, and each leg portion along with nipping portions configured to support the lens portion, wherein each leg portion has flexibility and includes a first bent portion, a second bent portion, a linear root portion, a linear intermediate portion, and a linear front end portion, wherein the linear root portion extends backward from a back side of the lens portion and away from the lateral and the back sides from the limbus of the lens portion to the first bent portion;

the linear intermediate portion extends from the first bent portion forward and away from the back side, past the front side, and away from the lateral side to the second bent portion, and the linear front end portion extends from the second bent portion substantially parallel to the lens portion and away from the lateral side of the lens portion; and wherein the front end portion of each leg portion is configured to ben and come into contact with an inside of a ciliary sulcus of the human eye when the intraocular lens is placed in the rear section of the human eye.

8. The intraocular lens according to claim 7, wherein the first and the second arms of the first and the second nipping portions are curved at a half portion thereof.

9. The intraocular lens according to claim 7, wherein the first and the second arms of the first and second nipping portions each have front ends that are configured to contact each other and configured to nip a rear section of the iris when placed in the rear section of the human eye.

\* \* \* \* \*